US010932675B2

(12) United States Patent
Lu et al.

(10) Patent No.: US 10,932,675 B2
(45) Date of Patent: Mar. 2, 2021

(54) AIR CIRCUIT STRUCTURE, BLOOD PRESSURE MEASURING INSTRUMENT THEREOF, AND AIR CIRCUIT BOX

(71) Applicant: Shenzhen Mindray Bio-Medical Electronics Co., Ltd., Shenzhen (CN)

(72) Inventors: Yi Lu, Shenzhen (CN); Wenjun Hou, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 559 days.

(21) Appl. No.: 15/641,032

(22) Filed: Jul. 3, 2017

(65) Prior Publication Data

US 2017/0311814 A1 Nov. 2, 2017

Related U.S. Application Data

(63) Continuation of application No. PCT/CN2015/070129, filed on Jan. 1, 2015.

(51) Int. Cl.

| | |
|---|---|
| ***A61B 5/021*** | (2006.01) |
| ***A61B 5/022*** | (2006.01) |
| ***A61B 5/0225*** | (2006.01) |
| ***A61B 5/00*** | (2006.01) |
| *A61B 5/0235* | (2006.01) |

(52) U.S. Cl.

CPC ............ *A61B 5/021* (2013.01); *A61B 5/0225* (2013.01); *A61B 5/02141* (2013.01); *A61B 5/02208* (2013.01); *A61B 5/6824* (2013.01); *A61B 5/0235* (2013.01)

(58) Field of Classification Search

None

See application file for complete search history.

(56) References Cited

U.S. PATENT DOCUMENTS

| | | | | |
|---|---|---|---|---|
| 6,004,816 | A | 12/1999 | Mizukami et al. | |
| 2004/0225224 | A1* | 11/2004 | Tseng | A61B 5/02141 600/499 |
| 2007/0142731 | A1* | 6/2007 | Ye | A61B 5/0225 600/494 |
| 2011/0066044 | A1* | 3/2011 | Moon | A61B 5/02125 600/485 |

FOREIGN PATENT DOCUMENTS

| | | | |
|---|---|---|---|
| CN | 1844922 | A | 10/2006 |
| CN | 101236194 | A | 8/2008 |
| CN | 101750476 | A | 6/2010 |
| CN | 101086473 | B | 9/2010 |
| CN | 101846671 | A | 9/2010 |
| CN | 102033122 | A | 4/2011 |
| CN | 103492875 | A | 1/2014 |
| WO | PCT/CN2014/095905 | | 12/2014 |

* cited by examiner

*Primary Examiner* — Marjan Fardanesh

(74) *Attorney, Agent, or Firm* — Kory D. Christensen

(57) ABSTRACT

An air circuit structure comprises the air circuit box, an air charging pump, a cuff air nozzle, air discharging valves and an air pressure examination sensor. The air circuit box comprises a shell with a cavity formed inside. The shell is provided with an access port, an air charging port and an air inlet port spaced apart, and the access port, the air charging port and the air inlet port are all connected to the cavity.

12 Claims, 9 Drawing Sheets

200
300
180
100

AIR CIRCUIT STRUCTURE, BLOOD PRESSURE MEASURING INSTRUMENT THEREOF, AND AIR CIRCUIT BOX

CROSS-REFERENCE TO RELATED APPLICATIONS

This application is a continuation of Patent Cooperation Treaty (PCT) Application No. PCT/CN2015/070129, filed Jan. 1, 2015, for "Air Circuit Structure, Blood Pressure Measuring Instrument Thereof, and Air Circuit Box," which is incorporated herein by reference.

TECHNICAL FIELD

The present disclosure relates to air circuit structures, blood pressure measuring instruments using these structures, and air circuit boxes.

SUMMARY

According to a first aspect, the present disclosure provides an air circuit structure used in a blood pressure measuring instrument, which may include: an air circuit box comprising a shell, wherein a cavity is formed inside the shell, the shell is provided with an access port, an air charging port and an air inlet port spaced apart, and the access port, the air charging port and the air inlet port are all connected to the cavity; an air charging pump comprising an air charging interface, wherein the air charging interface is directly connected to the air charging port; a cuff nozzle directly connected to the access port; an air discharging valve arranged on the shell and directly connected to the air inlet port; and an air pressure detecting sensor, provided with an interface, wherein the interface of the air pressure detecting sensor is directly connected to the cavity of the shell.

In one embodiment, the cuff nozzle is provided with a plug end, the plug end is inserted into and connected to the access port of the shell, the air charging interface is inserted into and connected to the air charging port of the shell, the shell is further provided with a first interface and a second interface connected to the cavity, the air circuit structure further comprises an overpressure detecting sensor, the overpressure detecting sensor is provided with an interface, and the interface of the over pressure detecting sensor and the interface of the air pressure detecting sensor are respectively inserted into and connected to the first interface and the second interface.

In one embodiment, the air inlet port comprises a first air inlet port and a second air inlet port spaced apart, the air discharging valve comprises a slow discharging valve and a quick discharging valve spaced apart, one end of the slow discharging valve is provided with a connecting port inserted into and connected to the first air inlet port, and one end of the quick discharging valve is provided with a connecting port inserted into and connected to the second air inlet port.

In one embodiment, the air circuit box is made of hard plastic material, and the air charging interface of the air charging pump, the plug end of the cuff nozzle, the connecting port of the slow discharging valve, the connecting port of the quick discharging valve, the interface of the overpressure detecting sensor and the interface of the air pressure detecting sensor are respectively interference fitted with the air charging port, the access port, the first air inlet port, the second air inlet port, the first interface and the second interface.

In one embodiment, the air charging port, the access port, the first air inlet port, the second air inlet port, the first interface and the second interface are made of flexible material or provided with flexible material surrounding a periphery thereof.

In one embodiment, one side of the shell is provided with an opening and a cover covering the opening, the opening is in communication with the cavity, a barrier is arranged in the cavity of the shell surrounding the first interface and the second interface, the barrier is provided with an air outlet, and the air outlet is away from the access port of the shell, the first air inlet port and the second air inlet port.

In one embodiment, the air circuit box further comprises a supporting portion extending outward at one end of the shell, the supporting portion comprises a first supporting portion and a second supporting portion spaced apart, the slow discharging valve and the quick discharging valve are respectively arranged on the first supporting portion and the second supporting portion, a first stop block and a second stop block, respectively corresponding to the first supporting portion and the second supporting portion, are protruded at the one end of the shell, the first air inlet port is formed on the first stop block, the second air inlet port is formed on the second stop block, and the first air inlet port and the second air inlet port respectively face the first supporting portion and the second supporting portion.

In one embodiment, two sides of the first supporting portion and the second supporting portion are respectively provided with bent edges away from each other, a separating edge is arranged between the first supporting portion and the second supporting portion, a first housing portion is formed between a bent edge of the first supporting portion and the separating edge, a second housing portion is formed between a bent edge of the second supporting portion and the separating edge, the slow discharging valve is housed in the first housing portion, and the quick discharging valve is housed in the second housing portion.

In one embodiment, one end of the first supporting portion away from the shell is bent to form a stop edge, a notch is arranged on the stop edge, the stop edge is divided into two stop ends, and the slow discharging valve is stopped at the two stop ends and partially extended out of the notch.

In one embodiment, one end of the bent edge of the second supporting portion away from the shell is extended toward the first supporting portion to form a hook, one end of the second supporting portion away from the shell is provided with a stop end, one end of the quick discharging valve away from the connecting port thereof is provided with a stop bump, the stop bump is provided with a stop opening, the stop bump is stopped on the stop edge, and the hook is snapped into the stop opening of the quick discharging valve.

According to another aspect, the present disclosure provides a blood pressure measuring instrument that may include a body and a cuff connected to the body, wherein an air circuit structure and a main control electric circuit board are arranged in the body, the main control electric circuit board is electronically connected with the air charging pump, the overpressure detecting sensor, the air pressure detecting sensor and the air discharging valve, and the cuff is connected to the air circuit structure.

In one embodiment, the main control electric circuit board is mounted on the air circuit box by a snap connection, an interference column hole or a fastener.

In one embodiment, both the overpressure detecting sensor and the air pressure detecting sensor are provided with welding feet, and the welding feet of the overpressure detecting sensor and the air pressure detecting sensor are welded on the main control electric circuit board.

In one embodiment, one end of the air circuit box is provided with a bulge, the access port is formed on the bulge and extended along a length of the air circuit box, the air charging port is formed on the shell adjacent to the bulge, a positioning column is arranged on the bulge, two sides of one end of the shell adjacent to the bulge are provided with a clasp and a fixing column, the main control electric circuit board is provided with a positioning hole at one end, and provided with a stop notch at one side and a stop position at the other side, the positioning column of the shell is inserted into the positioning hole of the main control electric circuit board, the clasp is snapped onto the stop position, and the fixing column is fixed in the stop notch.

In one embodiment, the blood pressure measuring instrument is an electronic non-invasive blood pressure measuring instrument.

According to yet another aspect, the present disclosure provides an air circuit box that may include a shell, wherein a cavity is formed inside the shell, the shell is provided with an air charging port and an air inlet port spaced apart, the air charging port and the air inlet port are made of flexible material and connected with the cavity, the air charging port and the air inlet port are connected with corresponding air circuit components via an airtight fit.

In one of the embodiments, the air charging port is connected to an air charging pump, the air inlet port is connected to an air pressure detecting sensor, the shell is further provided with a connecting port spaced apart from the air charging port, the air inlet port, and the connecting port is made of flexible material and connected with the cavity, and the connecting port is connected with an air discharging valve via an airtight fit.

DETAILED DESCRIPTION

A blood pressure measuring instrument, such as an electronic non-invasive blood pressure (NIBP) measuring instrument, generally may include a cuff and an internal air circuit structure connected to the cuff. The internal air circuit structure may include an air charging pump, an electromagnetic air discharging valve, an air pressure sensor and the like, which are connected to the air circuit. The NIBP measuring instrument could automatically control the air charging pump to charge or discharging the cuff, and collect human pressures transferred through the cuff by the internal air circuit structure.

However, components of the internal air circuit structure are generally connected with each other by a plurality of air ducts and 2-way or 3-way connectors. Therefore, the internal air circuit structure of the NIBP measuring instrument is large in sizes, decentralized, and has low degree of integration. In addition, the internal air circuit structure is formed by scattered air ducts and connectors and has many air circuit connection points, therefore the reliability is low.

In order to facilitate the understanding to the objects, features and advantages of the present disclosure, the detailed description of the specific embodiments of the present disclosure will be made below with reference to the drawings. Many specific details will be described below so as to facilitate the understanding to the present disclosure. However, the present disclosure may be implemented by many ways other than those described herein. A person skilled in the art can make similar improvements without departing from the connotation of the present disclosure. Therefore, the present disclosure will not be limited by the specific embodiments described below.

Figure 1:
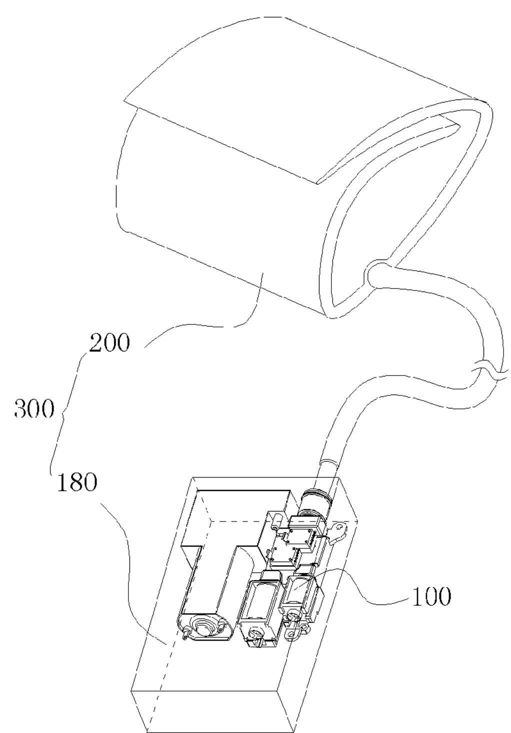
FIG. 1 is a perspective diagram of a blood pressure measuring instrument in one embodiment.
Figure 2:
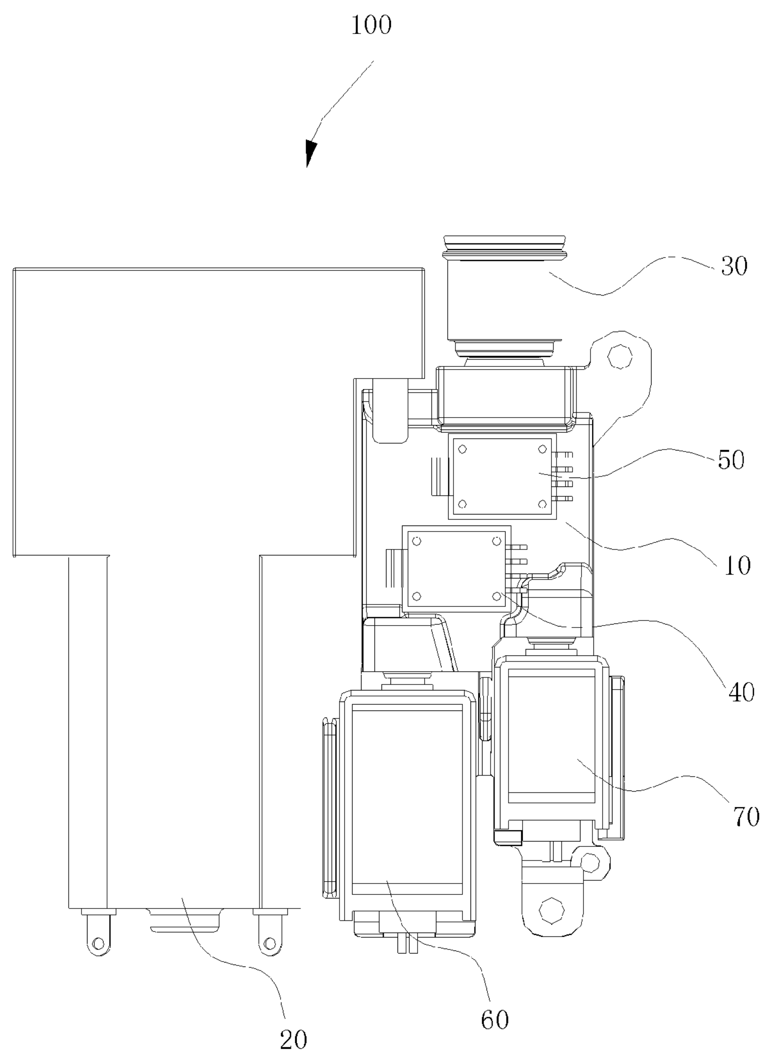
FIG. 2 is a diagram showing a front view of a air circuit structure of the blood pressure measuring instrument shown in FIG. 1.

Referring to FIG. 1 and FIG. 2, a blood pressure measuring instrument 300 may include a body 180 and a cuff 200 connected to the body 180. The body 180 may be internally provided with an air circuit structure 100 connected to the cuff 200 and a main control electric circuit board 80 (shown in FIG. 11) electrically connected with the air circuit structure 100. The air circuit structure 100 may include an air circuit box 10 and an air charging pump 20 connected to the air circuit box 10, a cuff air nozzle 30, an overpressure detecting sensor 40, an air pressure detecting sensor 50, a slow discharging valve 60 and a quick discharging valve 70. In the present embodiment, the blood pressure measuring instrument 300 may be a NIBP blood pressure measuring instrument.

Figure 3:
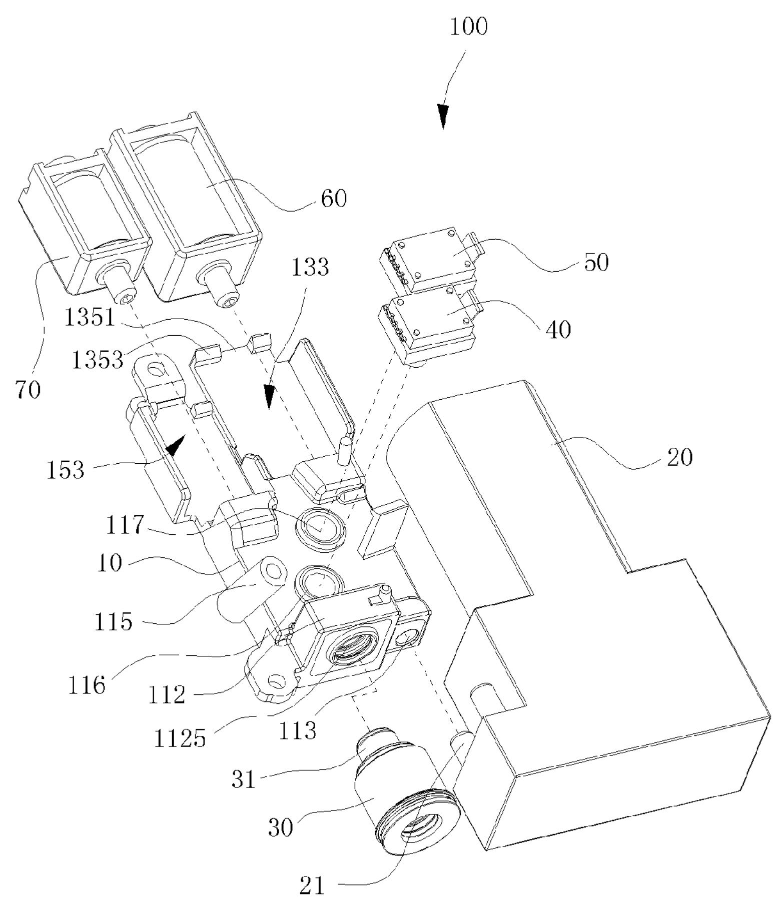
FIG. 3 is a diagram showing an explored perspective view of the air circuit structure shown in FIG. 2.
Figure 4:
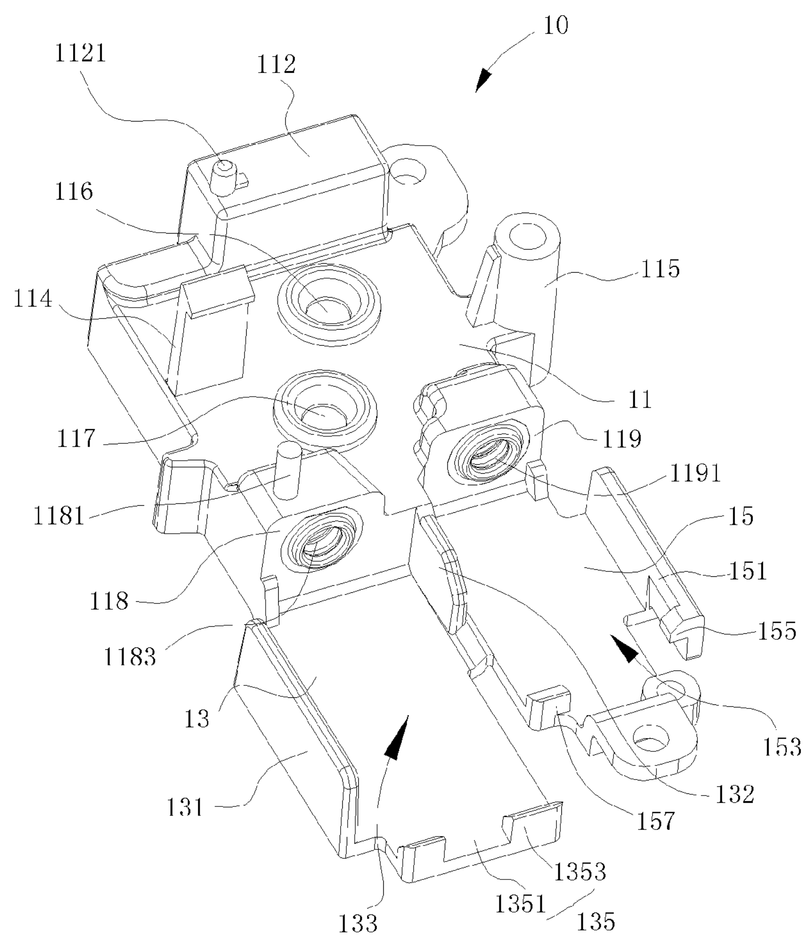
FIG. 4 is a perspective diagram of an air circuit box in the air circuit structure shown in FIG. 2.
Figure 5:
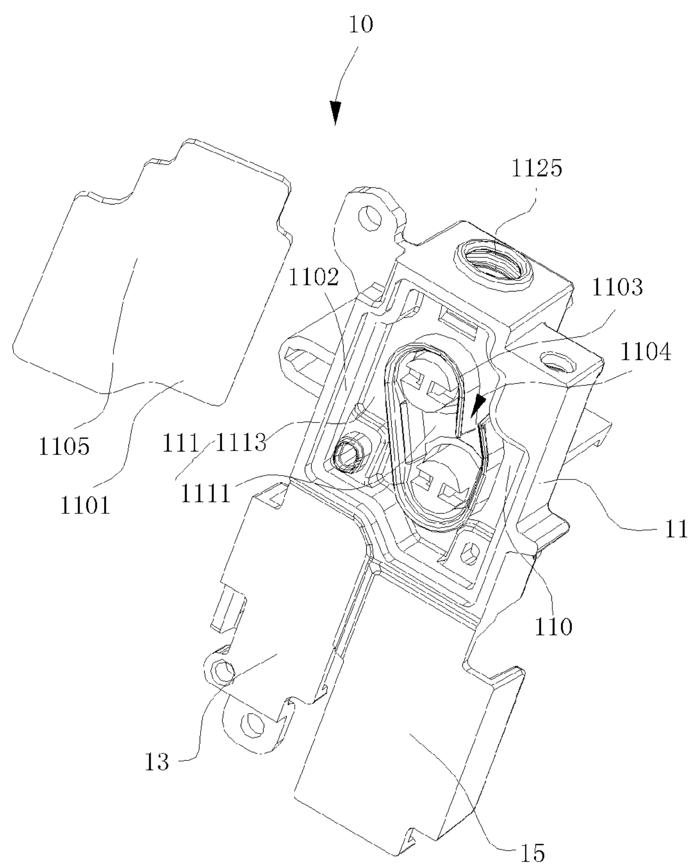
FIG. 5 is a diagram showing an exploded perspective view of the air circuit structure shown in FIG. 2 from another viewing angle.

Referring to FIGS. 3-5, the air circuit box 10 may be rectangle in shape, and may be a closed air box made of hard material, such as hard plastic. The air circuit box 10 may include a shell 11, a first supporting portion 13 and a second supporting portion 15 being parallel to and extending outwardly from one end of the shell 11.

As shown in FIG. 5, the shell 11 may have substantially a square body, and a cavity 111 may be formed therein. The end of the shell 11 away from the first supporting portion 13 may be provided with a bulge 112, and an air charging port 113 may be arranged at the side adjacent to the bulge 112. Both sides of an end of the shell 11 adjacent to the bulge 112 may be provided with a clasp 114 and a fixing column 115, respectively. A first interface 116 and a second interface 117 may be arranged between the clasp 114 and the fixing column 115. A first stop block 118 and a second stop block 119 may be protruded at the end of the shell 11 adjacent to the first supporting portion 13 and the second supporting portion 15. The side of the shell 11 opposite to the first interface 116 and the second interface 117 may be provided with an opening 110, and a cover 1101 covering the opening 110. A circle of barrier 1103 may be arranged in the cavity 111 of the shell 11 surrounding the first interface 116 and the second interface 117.

The bulge 112 may be provided with a positioning column 1121 and an access port 1125, which is connected to the cavity 111. The access port 1125 may be extended along the length of the air circuit box 10. The air charging port 113 may be connected to the cavity 111. The fixing column 115 may be a plastic column. A line connecting centers of the first interface 116 and the second interface 117 may obliquely intersect with a length direction of the air circuit box 10. A first stop block 118 and a second stop block 119 may be located at the end of the shell 11 adjacent to the first supporting portion 13 and the second supporting portion 15. The first stop block 118 may be provided with a support column 1181, and a first air inlet port 1183 facing the first supporting portion 13. The top of the support column 1181 may be flushed with the top of the fixing column 115. The second stop block 119 may be provided with a second air inlet port 1191 facing the second supporting portion 15. Both the first air inlet port 1183 and the second air inlet port 1191 may be connected to the cavity 111.

The opening 110 may connect the cavity 111 to outside. A step-like stop surface 1102 may be formed surrounding a periphery of the cavity. The barrier 1103 may divide the cavity 111 into an inner ring 1111 and an outer ring 1113. The barrier 1103 may further be provided with an air outlet 1104 to connect the inner ring 1111 to the outer ring 1113. The air outlet 1104 may be away from the access port 1125, the first air inlet port 1183 and the second air inlet port 1191 of the shell 11, thereby reducing a direct influence of airflow disturbance generated by charging and releasing of the air charging pump 20, the slow discharging valve 60 and the quick discharging valve 70 in the outer ring 1113 of the cavity 111 to the overpressure detecting sensor 40 and the air pressure detecting sensor 50 in the inner ring 111. A sealing surface 1105 may be arranged on one side of the cover 1101. The sealing surface 1105 may be fitted with the stop surface 1102 so as to seal the opening 110. In the present embodiment, the cover 1101 may be sealed with the opening 110 by glue or ultrasonic welding. In the present embodiment, the air charging port 113, the access port 1125, the first interface 116, the second interface 117, the first air inlet port 1183 and the second air inlet port 1191 of the shell 11 may all be made of flexible material or provided with flexible material around the periphery of their own so as to achieve the sealing. The flexible material may be flexible plastic or silicone or silicone gel material.

Both the first supporting portion 13 and the second supporting portion 15 may be plate-like. Two sides of the first supporting portion 13 and the second supporting portion 15 which are away from each other may be respectively provided with bent edges 131, 151 extending vertically. A separating edge 132 may be arranged between the first supporting portion 13 and the second supporting portion 15. The bent edges 131, 151 and the separating edge 132 may all be located on the side opposite to the opening 110. A first housing portion 133 may be formed between the bent edge 131 and the separating edge 132, and a second housing portion 153 may be formed between the bent edge 151 and the separating edge 132. An end of the bent edge 151 away from the shell 11 may be extended toward the bent edge 131 to form a hook 155. An end of the first supporting portion 13 away from the shell 11 may be bent to form a stop edge 135. A notch 1351 may be arranged at a center of the stop edge 135 such that the stop edge 135 is divided into two first stop ends 1353. An end of the second supporting portion 15 away from the shell 11 may be provided with a second stop end 157. The second stop end 157 may be located at a side of the second supporting portion 15 adjacent to the first supporting portion 13 and extended toward the bent edge 131. The second stop end 157 and the separating edge 132 may be spaced apart from each other.

Figure 6:
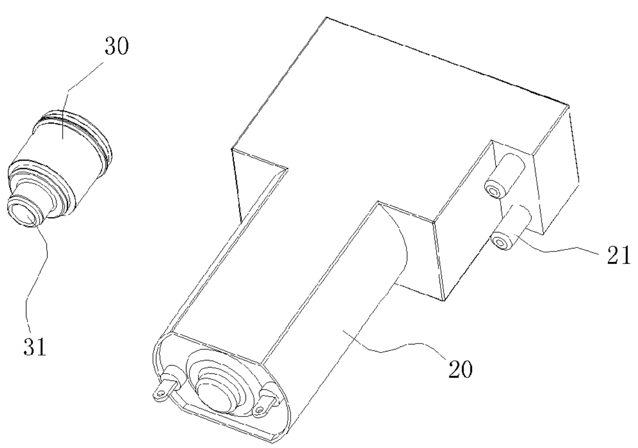
FIG. 6 is a perspective diagram of an air charging pump and a cuff nozzle of the air circuit structure shown in FIG. 2.

Referring to FIG. 6, the air charging pump 20 may be arranged at one side of the shell 11, and directly connected with the shell 11. The air charging pump 20 may be provided with an air charging interface 21 which may be detachably inserted into and connected with the air charging port 113 of the shell 11. The flexible sealing material on the air charging port 113 may enable an interference sealing fit between the air charging interface 21 and the air charging port 113. The air charging port 113 may correspondingly charge the outer ring 1113 of the cavity 111.

The cuff air nozzle 30 may be directly connected to one end of the shell 11. A plug end 31 may be arranged on the cuff air nozzle 30. The plug end 31 may be detachably inserted into and connected to an access port 1125 of the shell 11 so as to connect the cuff air nozzle 30 to the air circuit box 10. The flexible sealing material in the access port 1125 may enable an interference sealing fit between the plug end 31 and the access port 1125.

Figure 7:
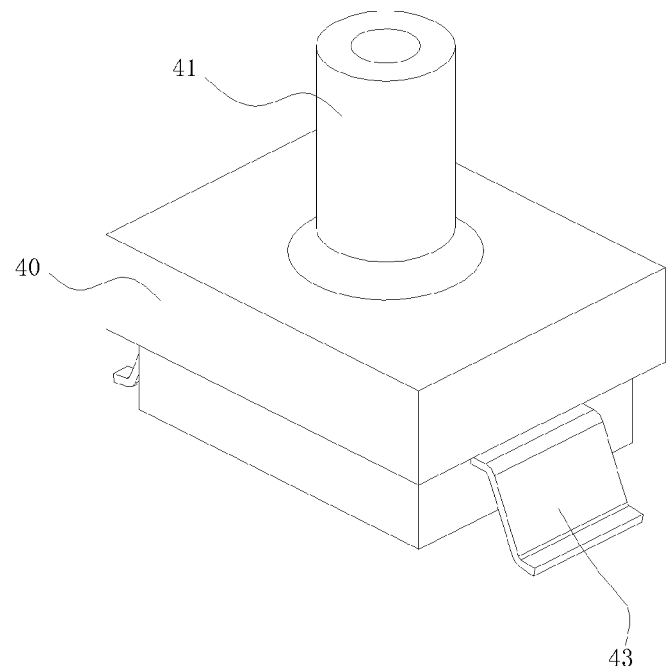
FIG. 7 is a perspective diagram of an overpressure detecting sensor of the air circuit structure shown in FIG. 2.

Referring to FIG. 7, the overpressure detecting sensor 40 and the air pressure detecting sensor 50 may be arranged on the shell 11 side by side and directly connected to the shell 11. The overpressure detecting sensor 40 may be provided with an interface 41, and respectively provided welding feet 43 on both sides. The interface 41 of the overpressure detecting sensor 40 may be detachably inserted into and connected to the first interface 116 of the shell 11 so as to be in direct connection with the cavity 111. The flexible sealing material of the first interface 116 may enable an interference sealing fit between the overpressure detecting sensor 40 and the first interface 116. The welding feet 43 may be welded on the main control electric circuit board 80.

Figure 8:
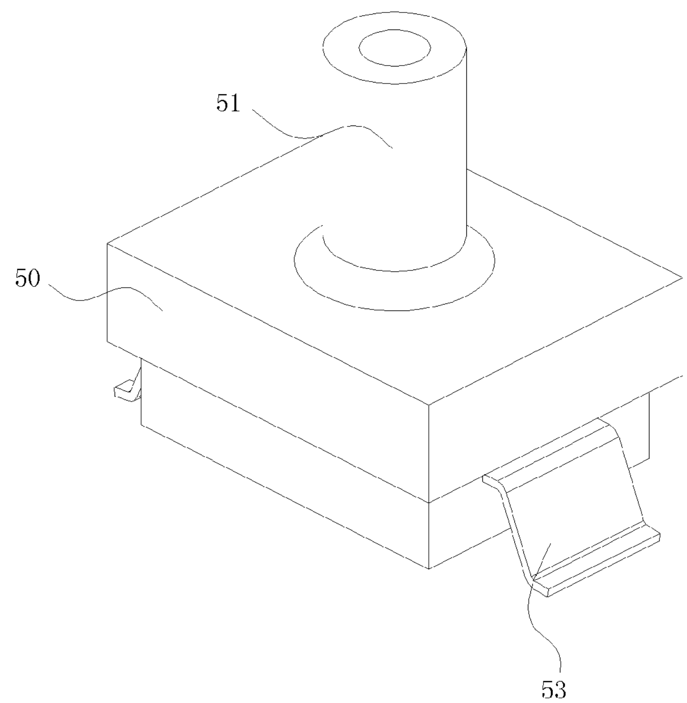
FIG. 8 is a perspective diagram of an air pressure detecting sensor of the air circuit structure shown in FIG. 2.

Referring to FIG. 8, the air pressure detecting sensor 50 may be provided with an interface 51, and respectively provided with welding feet 53 on both sides. The interface 51 of the air pressure detecting sensor 50 may be detachably inserted into and connected to the second interface 117 of the shell 11 so as to be in direct connection with the cavity 111. The flexible sealing material of the second interface 117 may enable an interference sealing fit between the air pressure detecting sensor 50 and the second interface 117. The welding feet 53 may be welded on the main control electric circuit board 80. The interface 41 of the overpressure detecting sensor 40 and the interface 50 of the air pressure detecting sensor 50 may be correspondingly located in the inner cavity 1111 of the cavity 111.

Figure 9:
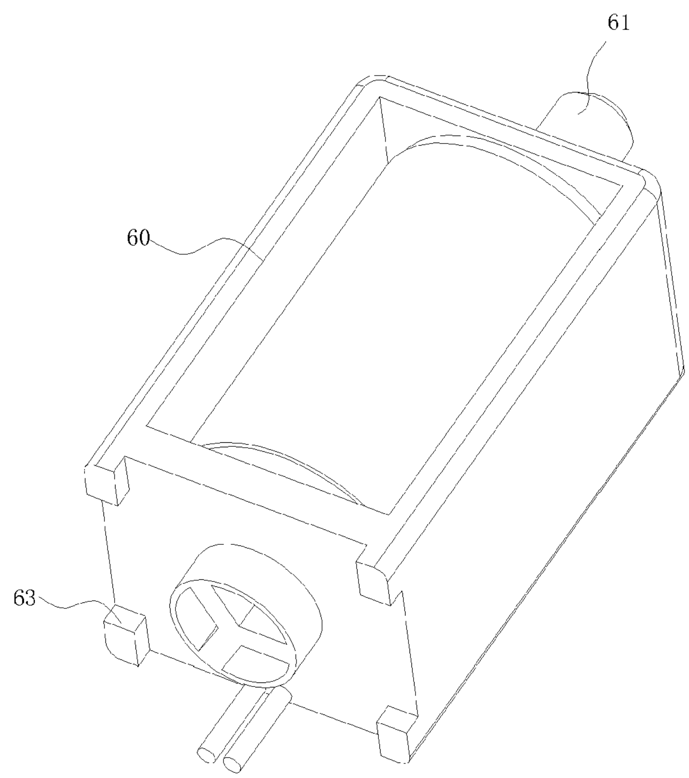
FIG. 9 is a perspective diagram of a slow discharging valve of the air circuit structure shown in FIG. 2.

Referring to FIG. 9, the slow discharging valve 60 may be housed in the first housing portion 133 and directly connected with to the shell 11. The slow discharging valve 60 may be provided with a connecting port 61 on one end, and stop bumps 63 on the a periphery of the other end. The connecting port 61 may be detachably inserted into and connected with the to a first air inlet port 1183. The flexible sealing material of the first air inlet port 1183 may enable an interference sealing fit between the slow discharging valve 60 and the air circuit box 10. The other end of the slow discharging valve 60 may be partially extended out of the notch 1351 of the shell 11. The stop bumps 63 may be stopped on the two first stop ends 1353.

Figure 10:
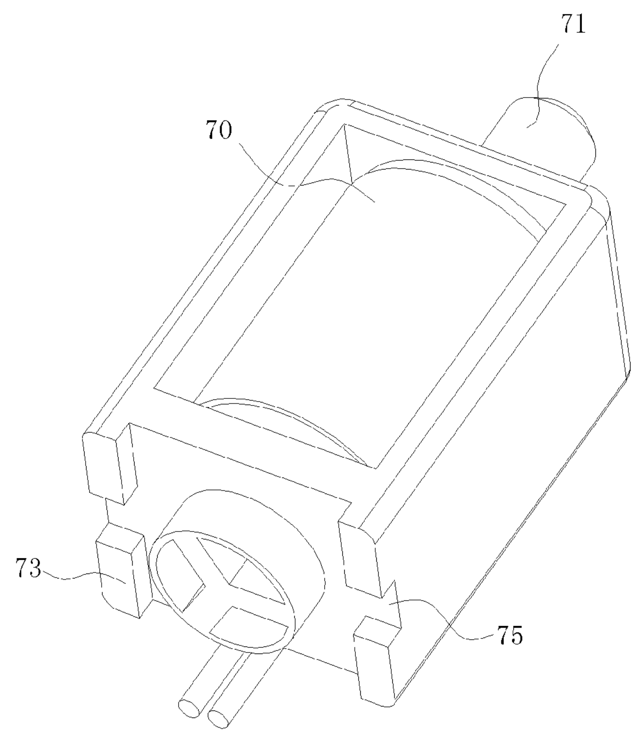
FIG. 10 is a perspective diagram of a quick discharging valve of the air circuit structure shown in FIG. 2.

Referring to FIG. 10, the quick discharging valve 70 may be housed in the second housing portion 153 and directly connected to the shell 11. The quick discharging valve 70 may be provided with a connecting port 71 on one end, and respectively provided with stop bumps 73 on both sides of the other end. The stop bumps 73 may be provided with stop openings 75. The connecting port 71 may be detachably inserted into and connected to the second air inlet port 1191. The flexible sealing material of the second air inlet port 1191 may enable an interference sealing fit between the quick discharging valve 70 and the air circuit box 10. The second stop end 157 may be stopped on one stop bump 73 of the quick discharging valve 70. The hook 155 of the second supporting portion 15 may be snapped into the stop opening 75 of the other stop bump 73. The connecting port 61 of the slow discharging valve 60 and the connecting port 71 of the quick discharging valve 70 may correspondingly discharging the air in the outer ring 1113 of the cavity 111.

Figure 11:
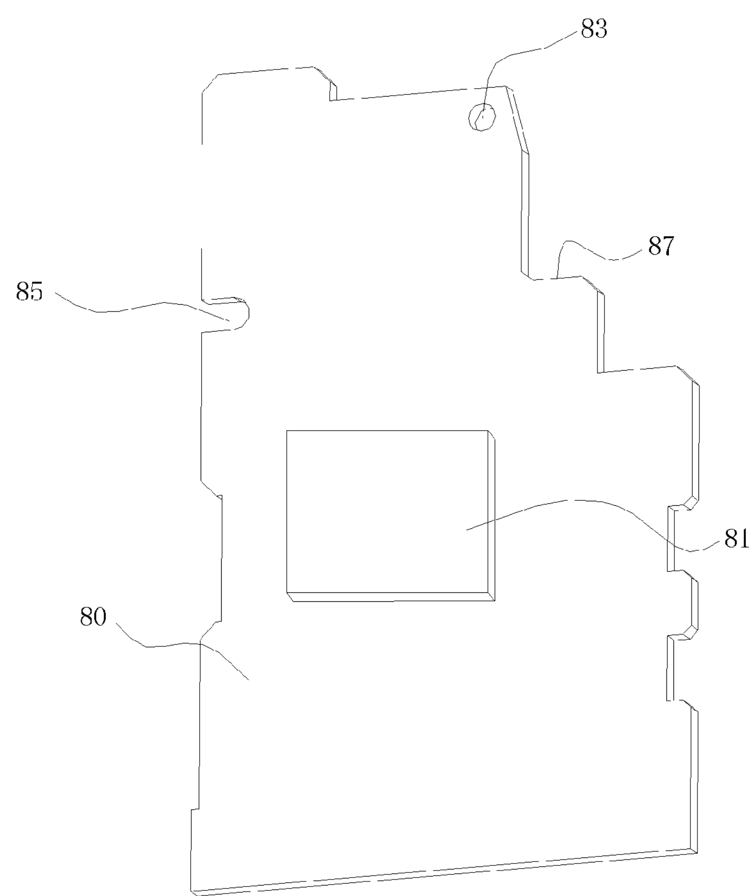
FIG. 11 is a perspective diagram of a main control electric circuit board of the air circuit structure shown in FIG. 2 in one embodiment.

Referring to FIG. 11, the main control electric circuit board 80 may be covered on the air circuit box 10. The main control electric circuit board 80 may be mounted on the air circuit box 10, for example, by snap connection or interference column or fastener. In the present embodiment, the main control electric circuit board 80 may include an electric circuit unit 81, a positioning hole 83 at a corner of the electric circuit unit 81, and a stop notch 85 on one side. A stop position 87 may further be arranged on one side of the main control electric circuit board 80 away from the stop notch 85. The electric circuit unit 81 may be electrically connected with the air charging pump 20, the overpressure detecting sensor 40, the air pressure detecting sensor 50, the slow discharging valve 60 and the quick discharging valve 70 so as to collect the data of the overpressure detecting sensor 40, the air pressure detecting sensor 50, the electrically control the air charging pump 20, the slow discharging valve 60 and the quick discharging valve 70. The positioning column 1121 of the shell 11 may be inserted into the positioning hole 83 of the main control electric circuit board 80, the clasp 114 may be snapped onto the stop position 87, and the fixing column 115 may be fixed at the periphery of the stop notch 85 by screws, so as to fix the main control electric circuit board 80 on the air circuit box 10, while the support column 1181 of the first stop block 118 may abut against the main control electric circuit board 80.

When assembling the blood pressure measuring instrument 300, the air charging pump 20 may be inserted into and connected to the access port 113 of the shell 11 such that the air charging pump 20 is located at one side of the air circuit box 10. The cuff air nozzle 30 may be inserted into and connected to the access port 1125 of the shell 11 such that the cuff air nozzle 30 is located at one end of the air circuit box 10. The overpressure detecting sensor 40 and the air pressure detecting sensor 50 may be respectively inserted into and connected to the first interface 116 and the second interface 117. The slow discharging valve 60 and the quick discharging valve 70 may be respectively inserted into and connected to the first air inlet port 1183 and the second air inlet port 1191. The main control electric circuit board 80 may be snapped onto the air circuit box 10, and the electric circuit unit 81 may be electrically connected with the air charging pump 20, the overpressure detecting sensor 40, the air pressure detecting sensor 50, the slow discharging valve 60 and the quick discharging valve 70. The air circuit structure 200 may be arranged in the body 180, and the cuff 200 may be connected to the cuff air nozzle 30.

When the blood pressure measuring instrument 300 is working, the main control electric circuit board 80 may control the air charging pump 20 to charge the air circuit box 10 and charge the cuff 200 through the cuff air nozzle 30, such that the cuff 200 is filled with air and inflated so as to closely abut against a human arm. The pressure in the cuff 200 may be increased rapidly in a short time and block the arterial blood flow. During this process, the overpressure detecting sensor 40 may detect whether an overpressure occurs in the cuff 200. The main control electric circuit board 80 may control the slow discharging valve 60 to begin to discharging the air to reduce the pressure. When the pressure in the cuff 200 is reduced to a pressure equal to the arterial blood pressure, the blood can flow through the arteries and thereby oscillation waves may be generated. The oscillation waves may propagate to the air pressure detecting sensor 50. The air pressure detecting sensor 50 may detect in real time the pressure and the fluctuation in the cuff 200. The pressure in the cuff 200 corresponding to the maximum amplitude of the oscillation waves may be equivalent to the mean arterial blood pressure. At this point, the detection ends. Then, the main control electric circuit board 80 may control the quick discharging valve 70 to discharging the air so as to relax the cuff 200.

The air circuit box 10 may be the core of the NIBP air circuit structure 100, which may directly connect, accommodate and fix the air charging pump 20, the cuff air nozzle 30, the overpressure detecting sensor 40, the air pressure detecting sensor 50, the slow discharging valve 60 and the quick discharging valve 70 such that the components above may be concentrated in the cavity 111 of the air circuit box 10 to achieve air pressure transmission, resulting in high integration. Furthermore, one air circuit box 10 is used to concentrate the air circuit connections of the components together, thus the number of connection points required by the air circuit connections between the existing dispersed components can be reduced. The air circuit may be effectively simplified, the complexity of the air circuit may be reduced, the size of the air circuit may be decreased, the possibility of leakage of the air circuit itself may be reduced, and the reliability of the connection may be increased.

The air circuit box 10 may be made of hard plastic material, therefore abnormalities, such as blockage caused by air circuit distortion, deformation, interference fit assembly, or the like, which often occurs in use in existing elastic connection air ducts, may be avoided. Therefore, assembly requirements may be significantly simplified, and a rate of qualified products may be increased. Furthermore, the access ports themselves of the air circuit box 10 may be provided with flexible sealing material, and no other sealing component is needed for the connection of each functional components. Therefore, assembly is easy, assembly steps are reduced, and the components may be effectively connected. The access ports could interference connected with the access ports of the components by the flexible sealing material. Therefore, the dimensional tolerance of the access ports of the components may be adapted so as to ensure air tightness.

The size of the blood pressure measuring instrument may be reduced through the compact air circuit structure of the NIBP air circuit structure 100. In addition, the integrated air circuit structure with the air circuit box 10 as the core has been modular. Therefore, it is very convenient to transplant in products, and the development speed of the products may be increased.

Figure 12:
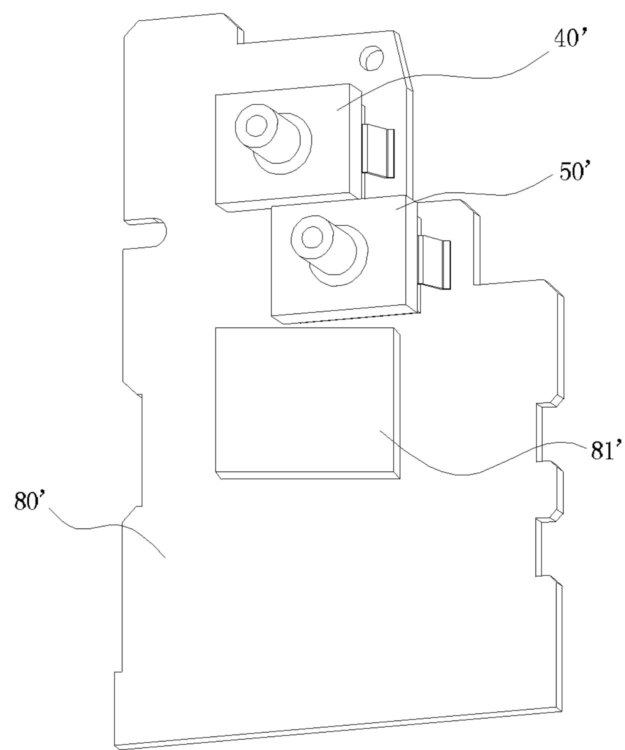
FIG. 12 is a perspective diagram of the main control electric circuit board of the air circuit structure in one embodiment.

Referring to FIG. 12, in another embodiment, an overpressure detecting sensor 40' and an air pressure detecting sensor 50' may be integrated on a main control electric circuit board 80' and electrically connected to an electric circuit unit 81'. The overpressure detecting sensor 40' and the air pressure detecting sensor 50' may be previously arranged on the main control electric circuit board 80' using surface mount or similar technologies, such as welding.

It may be understood that, in other embodiments, it may be possible to achieve the final discharging of the cuff 200 using only one slow discharging valve 60. In this case, the quick discharging valve 70 may be omitted, and the second stop block 119 of the shell 11 and the second support arm 15 may be omitted.

It may be understood that, in other embodiments, it is possible to achieve the measuring to the air pressure of the cuff using only one air pressure detecting sensor 50. In this case, the overpressure detecting sensor 40 may be omitted. That is, the air pressure detecting sensor 50 may simultaneously achieve the functions of measuring the air pressure and measuring the maximum protection air pressure. In this case, the first interface 116 on the shell 11 may be omitted. Specifically, when the blood pressure measuring instrument 300 has high enough system reliability or has other protection measures, it is possible to measure the air pressure of the air circuit system using only one air pressure detecting sensor 50. When the measured air pressure reach the upper limit of the working air pressure, stop charging and star blood pressure measuring can be started. That is, the air pressure detecting sensor 50 may simultaneously achieve the functions of measuring the air pressure measuring and measuring the maximum protection air pressure. In this case, the first interface 116 on the shell 11 can be omitted.

It may be understood that, in other embodiments, the air circuit box 10 may further be provided with a supporting portion connected to the shell 11 so as to accommodate and fix the air charging pump 20. It may be understood that, when the slow discharging valve 60 and the quick discharging valve 70 are able to be stably mounted on the shell 11, the first supporting portion 13 and the second supporting portion 15 may be omitted.

It may be understood that the shell 11 of the air circuit box 10 may be provided with an interface tube to replace the cuff nozzle 30. In other embodiments, the air circuit box 10 and the components may be designed as a whole, the components may be designed to have different placement positions, and the structural shape of the air circuit box 10 may be adjusted in order to adaptably fixedly connect the components. It may be understood that the components, such as the air charging pump, the discharging valves, the sensors and the air nozzle, may also be other types or kinds, such as other sensors sealed by front compression or other components needed to be added into the air circuit system. Alternatively, differentiated configurations may be implemented by changing the number of the components or reducing the connections of part of the components. In this situation, other traditional forms, such as silicone air ducts may be supplemented to connect the air circuit box 11 and the components which are not directly connected with the air circuit box 10.

It may be understood that, based on specific layout requirements of the measuring instrument, the air circuit box 10 may be divided into a plurality of parts each of which is connected to two or more components. The connections between the air circuit boxes 10 and the components may be implemented by traditional forms, such as silicone air ducts. The divide of the air circuit box 10 could reduce the connections of partial air circuit, and could also properly reduce nodes of the air circuit.

It may be understood that the access ports of the air circuit box 10 may be wholly made of flexible material other than being provided with flexible sealing material. The air circuit box 10 and the access port thereof may also be entirely made of hard material, such as hard plastic, and the access ports may be directly connected with the access ports of the components with an interference sealing. The air circuit box 10 may be entirely made of hard material, such as plastic, and other flexible material such as flexible plastic or silicone, etc. (for example, O-ring) may be used at the access ports to facilitate the sealing connection between the air circuit box 10 and the access ports of the components, which may be equivalent to the combination of the hard and soft plastics of the air circuit box 10 in function.

It may be understood that, based on needs, the air circuit box 10 may be modified as a combination of one box body and a plurality of covers or a combination of a plurality of box bodies and a plurality of covers. In addition, the access ports of the components may be arranged on the box body or the cover based on needs. The air circuit box 10 may be divided into parts for structure fixation and parts for air circuit connection, and a number of the parts may be two or more. The parts for structure fixation may integrally fix the pumps, the valves, the sensors or similar components, and the parts for air circuit connection may be in form of a single air container and multiple outlets, so as to connect to the nearest components. In a modified solution, the air circuit box 10 may be connected to the pumps, the valves, the sensors or other components to form an air circuit system. A preliminary hole-shaft connection between the components and the interfaces of the air circuit box 10 may be formed. In addition, the fixation of the air circuit system may be achieved by adding other components or upper and lower shells of the product.

It may be understood that it is possible that the air circuit box 10 is only provided with the air charging port 113 and the first air inlet port 1183, or the air charging port 113 and the first interface 116 (used for detecting the air pressure). The first air inlet port 1183 and the first interface 116 are the connecting ports for achieving respective functions. Of course, the air circuit box 10 may further be provided with a plurality of connecting ports for other functions, i.e. function interface.

Several embodiments of the present disclosure have been described above. The description is relatively specific and detailed. However, it could not be interpreted as limitation to the scope of the present disclosure. It should be noted that, for a person ordinarily skilled in the art, many modifications and improvements may be made without departing from the concepts of the present disclosure, all of which are within the scope of the present disclosure. Therefore, the protection scope of the present disclosure should be determined by the appended claims.

The invention claimed is:

1. An air circuit structure, used in a blood pressure measuring instrument, comprising:

an air circuit box comprising a shell, wherein a cavity is formed inside the shell, the shell is provided with an access port, an air charging port and an air inlet port spaced apart, and the access port, the air charging port, and the air inlet port are all connected to the cavity;

an air charging pump comprising an air charging interface, wherein the air charging interface is directly mated with the air charging port;

a cuff nozzle, directly mated with the access port;

an air discharging valve, arranged on the shell and directly mated with the air inlet port; and an air pressure detecting sensor, provided with an interface, wherein the interface of the air pressure detecting sensor is directly mated with the cavity of the shell;

wherein the cuff nozzle is provided with a plug end, the plug end is inserted into and connected to the access port of the shell, the air charging interface is inserted into and connected to the air charging port of the shell, the shell is further provided with a first interface and a second interface connected to the cavity, the air circuit structure further comprises an overpressure detecting sensor, the overpressure detecting sensor is provided with an interface, and the interface of the over pressure detecting sensor and the interface of the air pressure detecting sensor are respectively inserted into and connected to the first interface and the second interface;

wherein the air inlet port comprises a first air inlet port and a second air inlet port spaced apart, the air discharging valve comprises a slow discharging valve and a quick discharging valve spaced apart, one end of the slow discharging valve is provided with a connecting port inserted into and connected to the first air inlet port, and one end of the quick discharging valve is provided with a connecting port inserted into and connected to the second air inlet port;

wherein the air circuit box further comprises a supporting portion extending outward at one end of the shell, the supporting portion comprises a first supporting portion and a second supporting portion spaced apart, the slow discharging valve and the quick discharging valve are respectively arranged on the first supporting portion and the second supporting portion, a first stop block and a second stop block, respectively corresponding to the first supporting portion and the second supporting portion, are protruded at the one end of the shell, the first air inlet port is formed on the first stop block, the second air inlet port is formed on the second stop block, and the first air inlet port and the second air inlet port respectively face the first supporting portion and the second supporting portion.

2. The air circuit structure of claim 1, wherein two sides of the first supporting portion and the second supporting portion are respectively provided with bent edges away from each other, a separating edge is arranged between the first supporting portion and the second supporting portion, a first housing portion is formed between a bent edge of the first supporting portion and the separating edge, a second housing portion is formed between a bent edge of the second supporting portion and the separating edge, the slow discharging valve is housed in the first housing portion, and the quick discharging valve is housed in the second housing portion.

3. The air circuit structure of claim 2, wherein one end of the bent edge of the second supporting portion away from the shell is extended toward the first supporting portion to form a hook, one end of the second supporting portion away from the shell is provided with a stop end, one end of the quick discharging valve away from the connecting port thereof is provided with a stop bump, the stop bump is provided with a stop opening, the stop bump is stopped at the stop edge, and the hook is snapped into the stop opening of the quick discharging valve.

4. The air circuit structure of claim 1, wherein one end of the first supporting portion away from the shell is bent to form a stop edge, a notch is arranged on the stop edge, the stop edge is divided into two stop ends, and the slow discharging valve is stopped at the two stop ends and partially extended out of the notch.

5. The air circuit structure of claim 1, wherein the air circuit box is made of a hard plastic material, and the air charging interface of the air charging pump, the plug end of the cuff nozzle, the connecting port of the slow discharging valve, the connecting port of the quick discharging valve, the interface of the overpressure detecting sensor and the interface of the air pressure detecting sensor are respectively interference fitted with the air charging port, the access port, the first air inlet port, the second air inlet port, the first interface and the second interface.

6. The air circuit structure of claim 5, wherein the air charging port, the access port, the first air inlet port, the second air inlet port, the first interface and the second interface are made of a flexible material or provided with a flexible material surrounding a periphery thereof.

7. The air circuit structure of claim 1, wherein one side of the shell is provided with an opening and a cover covering the opening, the opening is in communication with the cavity, a barrier is arranged in the cavity of the shell surrounding the first interface and the second interface, the barrier is provided with an air outlet, and the air outlet is away from the access port of the shell, the first air inlet port and the second air inlet port.

8. A blood pressure measuring instrument, comprising an air circuit structure, used in a blood pressure measuring instrument, comprising:

an air circuit box comprising a shell, wherein a cavity is formed inside the shell, the shell is provided with an access port, an air charging port and an air inlet port spaced apart, and the access port, the air charging port, and the air inlet port are all connected to the cavity;

an air charging pump comprising an air charging interface, wherein the air charging interface is directly mated with the air charging port;

a cuff nozzle, directly mated with the access port;

an air discharging valve, arranged on the shell and directly mated with the air inlet port; and an air pressure detecting sensor, provided with an interface, wherein the interface of the air pressure detecting sensor is directly mated with the cavity of the shell;

wherein the cuff nozzle is provided with a plug end, the plug end is inserted into and connected to the access port of the shell, the air charging interface is inserted into and connected to the air charging port of the shell, the shell is further provided with a first interface and a second interface connected to the cavity, the air circuit structure further comprises an overpressure detecting sensor, the overpressure detecting sensor is provided with an interface, and the interface of the over pressure detecting sensor and the interface of the air pressure detecting sensor are respectively inserted into and connected to the first interface and the second interface;

wherein the air inlet port comprises a first air inlet port and a second air inlet port spaced apart, the air discharging valve comprises a slow discharging valve and a quick discharging valve spaced apart, one end of the slow discharging valve is provided with a connecting port inserted into and connected to the first air inlet port, and one end of the quick discharging valve is provided with a connecting port inserted into and connected to the second air inlet port;

wherein the air circuit box further comprises a supporting portion extending outward at one end of the shell, the supporting portion comprises a first supporting portion and a second supporting portion spaced apart, the slow discharging valve and the quick discharging valve are respectively arranged on the first supporting portion and the second supporting portion, a first stop block and a second stop block, respectively corresponding to the first supporting portion and the second supporting portion, are protruded at the one end of the shell, the first air inlet port is formed on the first stop block, the second air inlet port is formed on the second stop block, and the first air inlet port and the second air inlet port respectively face the first supporting portion and the second supporting portion; and a body and a cuff connected to the body, wherein the air circuit structure and a main control electric circuit board is arranged in the body, the main control electric circuit board is electronically connected with the air charging pump, an overpressure detecting sensor, the air pressure detecting sensor and an air discharging valve, and the cuff is connected to the air circuit structure.

9. The blood pressure measuring instrument of claim 8, wherein the main control electric circuit board is mounted on the air circuit box by a snap connection, an interference column hole or a fastener.

10. The blood pressure measuring instrument of claim 9, wherein, both the overpressure detecting sensor and the air pressure detecting sensor are provided with welding feet, and the welding feet of the overpressure detecting sensor and the air pressure detecting sensor are welded on the main control electric circuit board.

11. The blood pressure measuring instrument of claim 9, wherein one end of the air circuit box is provided with a bulge, the access port is formed on the bulge and extended along a length of the air circuit box, the air charging port is formed on the shell adjacent to the bulge, a positioning column is arranged on the bulge, two sides of one end of the shell adjacent to the bulge are provided with a clasp and a fixing column, the main control electric circuit board is provided with a positioning hole at one end, and provided with a stop notch at one side and a stop position at the other side, the positioning column of the shell is inserted into the positioning hole of the main control electric circuit board, the clasp is snapped onto the stop position, and the fixing column is fixed in the stop notch.

12. The blood pressure measuring instrument of the claim 8, wherein the blood pressure measuring instrument is an electronic non-invasive blood pressure measuring instrument.

* * * * *